United States Patent [19]

Choksi et al.

[11] 4,046,145

[45] Sept. 6, 1977

[54] SYRINGE CONNECTOR

[75] Inventors: Pradip Vinobchandra Choksi, Northridge; Walter Seemayer, Burbank, both of Calif.

[73] Assignee: American Hospital Supply Corporation, Evanston, Ill.

[21] Appl. No.: 700,902

[22] Filed: June 29, 1976

[51] Int. Cl.$^2$ .................... A61M 5/00

[52] U.S. Cl. .................... 128/215; 128/272.3; 141/2; 141/27

[58] Field of Search .................... 128/215, 216, 218 R, 128/272, 272.3, 2 F; 141/2, 27, 326, 327, 382-386

[56] References Cited

U.S. PATENT DOCUMENTS

| | | | |
|---|---|---|---|
| 2,342,215 | 2/1944 | Perelson | 128/272 |
| 2,906,300 | 9/1959 | Becher | 141/357 X |
| 3,578,037 | 5/1971 | Flynn | 141/2 |
| 3,610,297 | 10/1971 | Raaf et al. | 141/27 |
| 3,729,031 | 4/1973 | Baldwin | 141/2 |

OTHER PUBLICATIONS

Female-to-Female Luer-Lock Connector, Catalog No. 3110 of Becton Dickinson.

*Primary Examiner*—John D. Yasko
*Attorney, Agent, or Firm*—Larry N. Barger

[57] ABSTRACT

A connector for joining a small dose syringe to a large reservoir syringe for filling the small dose syringe from the reservoir syringe. The connector has a tubular female-to-female coupler and there is a protector housing that is spaced radially outward from and extends forwardly beyond the coupler portion that attaches to the small dose syringe, thereby protecting this coupler portion from touch contamination. A removable closure with a recessed plug protects the small dose coupler portion from contamination when not in use.

18 Claims, 5 Drawing Figures

SYRINGE CONNECTOR

BACKGROUND OF THE INVENTION

In dispensing liquid medication, pharmacists will often extract liquid medication from a large bottle or vial into a reservoir syringe, such as a large 30 cc syringe, A series of small dose syringes, 3 cc for example, will be sequentially connected to the large reservoir syringe and filled from it. In the example given above, ten small dose syringes can be filled from one charge of the large reservoir syringe.

In the past there have been coupling devices for joining the small dose and reservoir syringe during this small dose syringe filling procedure. Some of these have been tubular metal couplers with a tapered female Luer sleeve at each end.

There was a problem with these previous tubular couplers because the end of the coupler used to repeatedly connect and disconnect the small dose syringe was exposed for touch contamination by the pharmacist connecting and disconnecting the series of small dose syringes. This could occur when he grasped the tubular coupler in one hand and the small dose syringe in the other to connect, or disconnect, the small dose syringe.

SUMMARY OF THE INVENTION

We have overcome the problem with the previous tubular couplers by providing a tubular coupler with a protector housing connected to the coupler and this housing is radially spaced outwardly from the coupler. The housing also extends forwardly beyond the coupler end that is connected and disconnected to the small dose syringe. Thus, the pharmacist can grasp the housing for manipulating the connecting and disconnecting of the small dose syringe without ever touching the tubular coupler itself. The housing portion that protrudes beyond the tubular coupler's forward end acts as a shield preventing inadvertent touching of the forward end of the tubular coupler.

Prior to connecting the small dose syringe to the tubular coupler, a removable closure with a protective skirt surrounding a recessed plug closes off the coupler's forward end to further protect against contamination.

DETAILED DESCRIPTION

Figure 1:
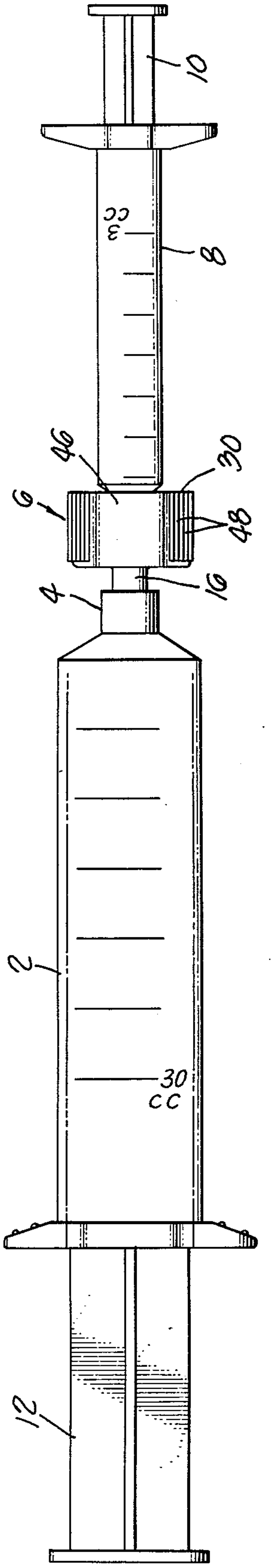
FIG. 1 is a front elevational view showing the large reservoir syringe connected to the small dose syringe by the connector of this invention.

Referring to FIG. 1, a large reservoir syringe 2 is filled from a medical liquid vial or bottle. In the drawings a conventional 30 cc syringe is shown as the reservoir syringe and has a conventional internally threaded Luer-lock collar 4. A rear portion of the connector of this invention, shown generically as 6, is connected to Luer-lock collar 4 of the reservoir syringe 2. A forward end of the connector 6 is attached to a small dose syringe 8. With the connection shown in FIG. 1, the small dose syringe can be filled from the reservoir syringe simply by pulling the plunger 10 of the small dose syringe to the right in FIG. 1. This method of filling the small dose syringe is preferred over a method of pushing a plunger 12 of the reservoir syringe to the right in FIG. 1. Pulling plunger 10 rather than pushing plunger 12 gives a more accurately controllable volume in the small dose syringe.

Figure 2:
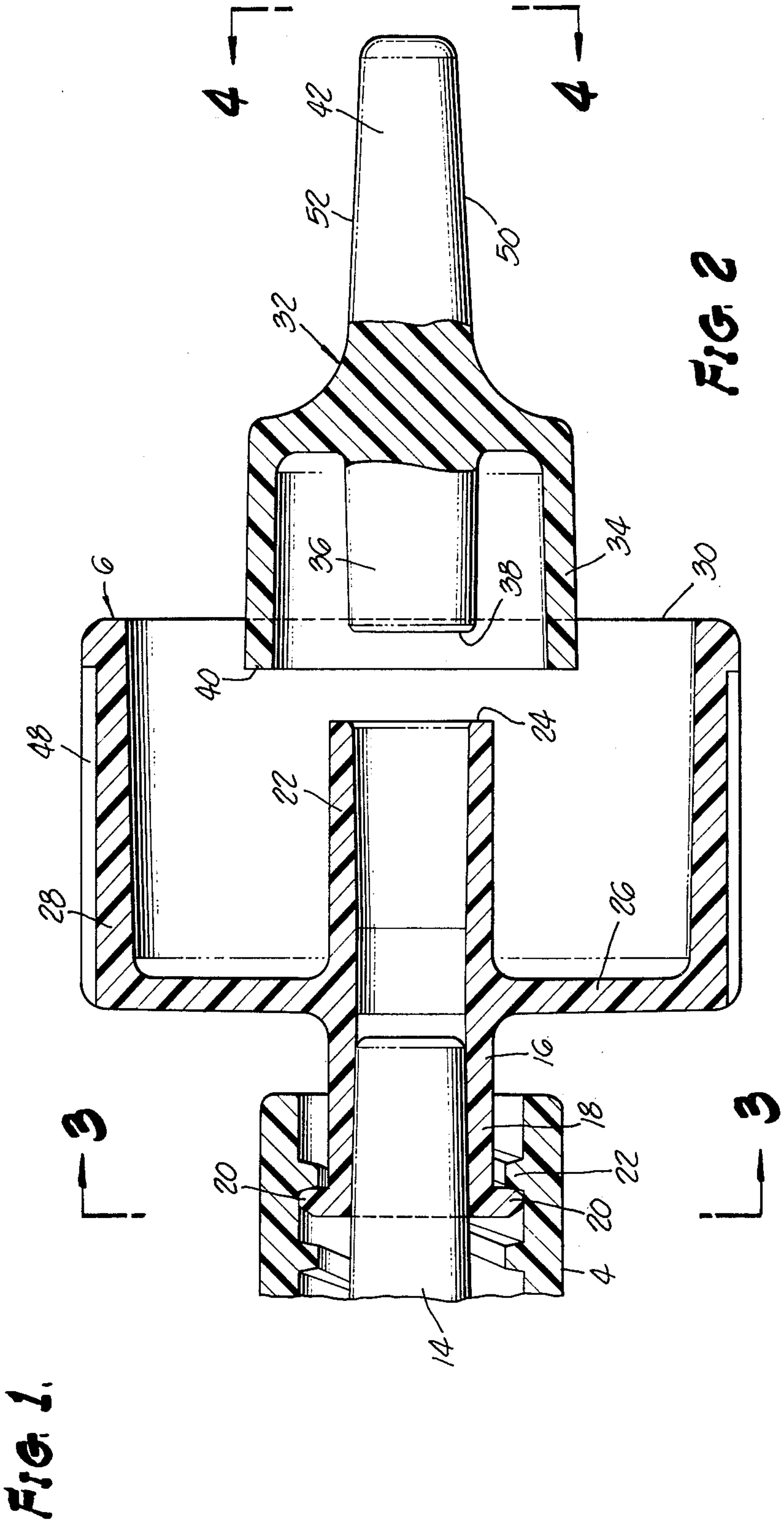
FIG. 2 is an enlarged sectional view of the connector showing one end joined to the reservoir syringe and a protective cap being removed from a forward portion of the connector.

As shown in more detail in FIG. 2, the Luer-lock collar 4 surrounds a tapered Luer adapter 14 as is conventional with syringes. The connector includes a tubular coupler 16 with a rear internally tapered female portion 18 that forms a removable liquid-type wedge seal with tapered adapter 14. Laterally protruding ears, such as 20 engage internal threads 22 of Luer-lock collar 4 securely holding tubular adapter to the reservoir syringe.

The tubular coupler has a forward end portion 22 with an internal tapered female Luer surface for wedging to a Luer adapter of small dose syringe 8. It is important that the critical forward end 24 of the tubular adapter not be contaminated during connecting and disconnecting a series of small dose syringes. This invention reduces the chance of touch contamination by providing a housing 6 that includes a transverse wall 26 joined to a central portion of tubular adapter 16. The transverse wall 26 is in turn joined to a protective collar 28 that is circumferentially spaced from a forward section 22 of the tubular coupler. Preferably, the outer surface of the protective collar has a diameter more than three times greater than the internal bore of the coupler's forward section 22. Also, the forward section 22 of the coupler is free of locking ears to engage with a Luer-lock collar of a syringe, so such syringe can be attached and detached with a simple axial motion. A forward end 30 of protective collar 28 will likely engage the pharmacist's hand or other object preventing it from touching critical front end 24 of the tubular adapter. This front end 24 might contain a liquid drop as a result of disconnecting the small dose syringe 8.

Figure 5:
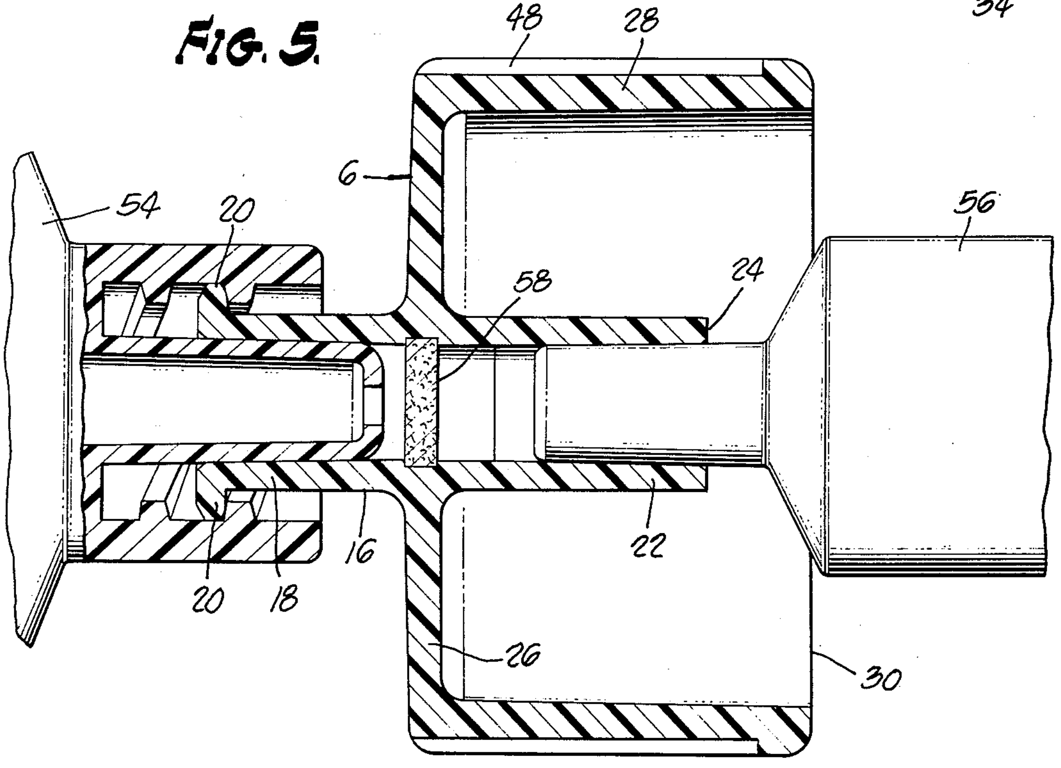
FIG. 5 is an enlarged sectional view of a second embodiment of the invention showing an optional filter in the tubular adapter.

Preferably, there is an annular recess between the protective collar 28 and forward section 22 of the coupler of sufficient size to receive a Luer-lock collar of a syringe without interferring contact between the two collars. The size of such Luer-lock collar is shown in FIG. 5.

Prior to connecting the small dose syringe 8, a protective closure shown generically as 32 closes off the forward end of the tubular coupler. This closure includes a protective skirt 34 that is circumferentially spaced outwardly from the forward portion 22 of the tubular coupler when the closure is assembled to the tubular coupler. Thus, skirt 34 does not touch the tubular coupler so as not to transfer contamination to and from such coupler. The closure is supported on forward end 22 of the coupler by a recessed plug 36 that is tapered to wedgingly fit the internal surface of the coupler's forward end portion 22. A rear portion 38 of plug 36 is recessed from a rear end 40 of skirt 34. Because the skirt's end 40 protrudes beyond the plug's rear end 38, the skirt acts to protect the plug's rear end 38 from contamination. To aid in connecting and disconnecting the closure, a flat handle 42 is provided.

Figure 3:
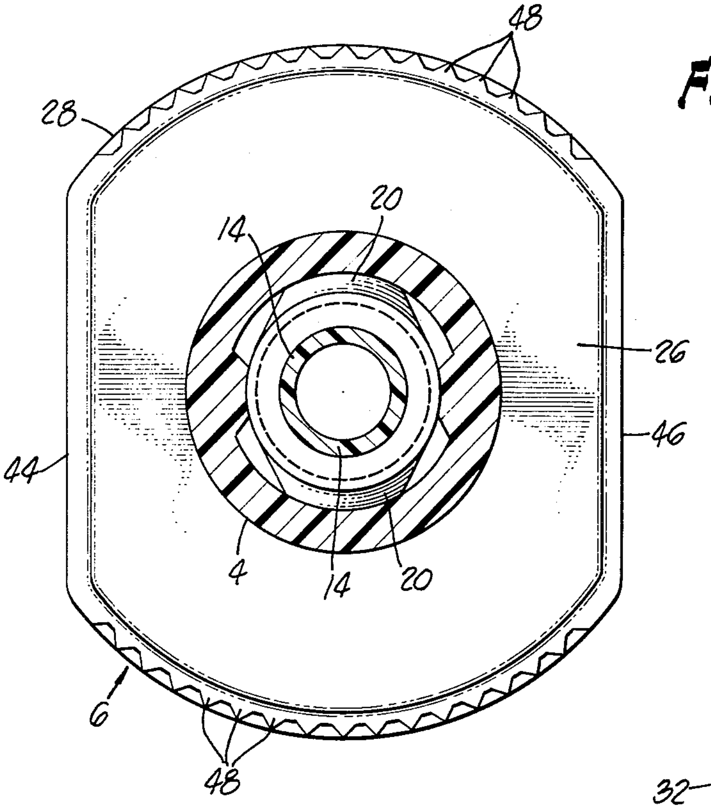
FIG. 3 is a sectional view taken along line 3—3 of FIG. 2.

In the sectional view of FIG. 3, the shape of the protective collar is more clearly shown. Here the collar 28 has a pair of flat sections 44 and 46 to prevent the connector from rolling on a flat surface. For improved gripping, the collar 28 also has a series of longitudinal ribs as indicated at 48.

Figure 4:
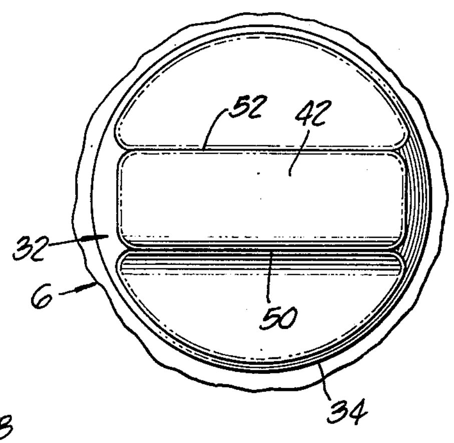
FIG. 4 is a sectional view taken along line 4—4 of FIG. 2.

The FIG. 4 view points out the shape of the closure's handle 42 which includes a pair of flat surfaces 50 and 52 for easy gripping.

In FIG. 5, the connector is shown attached to both a reservoir syringe 54 and a small dose syringe 56. In this FIGURE, a second embodiment of the connector is shown with an optional filter 58. Thus, particulate matter that might be within the large reservoir syringe is filtered out prior to its transfer to the small dose syringe 56. All other aspects of the second embodiment of the connector are the same as in the first embodiment.

This invention has worked very well when the connector is injection molded with the tubular coupler and the protector housing as an integral one-piece unit. Preferably, both the connector and closure are molded of a polypropylene thermoplastic which has a very high drug compatibility.

In the preceding description, specific embodiments have been used to describe this invention. However, it is understood by those skilled in the art that certain modifications can be made to these embodiments without departing from the spririt and scope of the invention.

We claim:

1. A connector for transfer of medical fluids comprising: a tubular coupler having an outer surface and including a front attaching means and a rear attaching means; a protector housing secured to the coupler, said housing having a collar with an inner surface which is spaced radially outward from the coupler, and the collar extends beyond a forward end of the front attaching means to protect it from contamination; and said protector housing including a spacer means fixedly connected to both the collar and tubular adapter to maintain the spacial relationship between the collar and tubular coupler.

2. A connector as set forth in claim 1, wherein the front attaching means is a female tapered tube section.

3. A connector as set forth in claim 1, wherein the rear attaching means is a female tapered tube section.

4. A connector as set forth in claim 3, wherein the rear attaching means includes one or more protruding ears for engaging with a Luer-lock collar of a syringe.

5. A connector for transfer of sterile medical liquids comprising: a tubular coupler with a front attaching means and a rear attaching means; a protector housing secured to the coupler, said housing having a collar which is spaced radially outward from the coupler and extends beyond a forward end of the front attaching means to protect it from contamination; and said housing includes a transverse wall secured to the tubular coupler and the collar is secured to said transverse wall.

6. A connector as set forth in claim 1, wherein the collar has at least one flat area to prevent the connector from rolling on a flat surface.

7. A connector as set forth in claim 1, wherein the collar has a surface means to prevent slippage when grasped by an operator.

8. A connector as set forth in claim 7, wherein the surface means includes a series of longitudinal ribs.

9. A connector as set forth in claim 1, wherein the connector includes a removable closure for protecting the front attaching means.

10. A connector as set forth in claim 9, wherein the closure includes a handle protruding outwardly beyond the collar when such closure is attached to the front attaching means.

11. A connector as set forth in claim 9, wherein the front attaching means is a female tapered tube section, and the closure includes a tapered plug wedgingly fitted within this female tapered tube section.

12. A connector as set forth in claim 11, wherein the closure includes a skirt which is spaced radially outwardly from both the plug and female tapered tube section when the closure's plug is inserted and wedgingly fit to the female tapered tube section.

13. A connector as set forth in claim 12, wherein the skirt extends longitudinally beyond the plug, thereby reducing the chance of touch contamination of the closure's plug.

14. A connector as set forth in claim 1, wherein the tubular coupler has a filter secured therein.

15. A connector for transfer of medical fluids comprising: a tubular coupler with an internal front coupling bore and a rear attaching means; a protector housing having a collar spaced outward from the tubular coupler, and this collar has opposed external gripping surfaces separated by the distance that is at least three times the diameter of the internal front coupling bore; and these gripping surfaces extend beyond a forward end of the front attaching means; and said protector housing has spacer means fixedly connected to both the collar and tubular adapter to maintain the spacial relationship between the collar and tubular adapter.

16. A connector as set forth in claim 15, wherein the connector has an annular recess between the protector housing collar and tubular coupler of sufficient size to receive a Luer-lock collar of a syringe without interferring contact between such Luer-lock collar and the protector housing collar.

17. A connector as set forth in claim 15, wherein the tubular coupler has a forward end portion of a diameter that does not interfer with simple axial attachment and detachment of a syringe with a Luer-lock collar.

18. An assembly for transferring medical fluids comprising: a large reservoir syringe; a small dose syringe; and a connector joining said two syringes together; said connector including a tubular coupler and protector housing with a collar circumferentially spaced outwardly from a connecting joint between the small dose syringe and the tubular coupler, said protector housing extending forwardly beyond the tubular coupler's forward end to provide protection for such forward end during connection and disconnection of the small dose syringe; and said protector housing including a spacer means fixedly connected to both the collar and tubular adapter to maintain the spacial relationship between the collar and tubular adapter, whereby the chance of touch contamination of the coupler during connecting and disconnecting of the small dose syringe is substantially reduced.

* * * * *